(12) United States Patent
Schmaus et al.

(10) Patent No.: US 10,022,310 B2
(45) Date of Patent: Jul. 17, 2018

(54) SYNERGISTIC MIXTURES OF AROMATIC ALCOHOLS AND DERIVATIVES THEREOF AND TROPOLONE (DERIVATIVES)

(75) Inventors: Gerhard Schmaus, Hoexter-Bosseborn (DE); Joachim Roeding, Badenweiler (DE); Ravikumar Pillai, Emerson, NJ (US); William Johncock, Reinbek (DE)

(73) Assignee: Symrise AG, Holzminden (DE)

( * ) Notice: Subject to any disclaimer, the term of this patent is extended or adjusted under 35 U.S.C. 154(b) by 2006 days.

(21) Appl. No.: 11/461,762

(22) Filed: Aug. 1, 2006

(65) Prior Publication Data
US 2007/0054967 A1     Mar. 8, 2007

Related U.S. Application Data

(63) Continuation-in-part of application No. PCT/EP2006/063264, filed on Jun. 16, 2006.
(Continued)

(51) Int. Cl.
*A61K 47/00* (2006.01)
*A61K 8/34* (2006.01)
(Continued)

(52) U.S. Cl.
CPC .............. *A61K 8/34* (2013.01); *A01N 35/06* (2013.01); *A61K 8/347* (2013.01); *A61K 8/35* (2013.01);
(Continued)

(58) Field of Classification Search
CPC .............................. A01N 43/90; C07D 495/04
(Continued)

(56) References Cited

U.S. PATENT DOCUMENTS 2,770,546 A * 11/1956 Thompson ..................... 426/546
4,950,686 A *  8/1990 Kondo et al. ................. 514/546
(Continued)

FOREIGN PATENT DOCUMENTS

FR   2 747 572 A1   10/1997
JP   02-243607 A     9/1990
(Continued)

OTHER PUBLICATIONS

Trust, "Antibacterial Activity of Tropolone," Antimicrobial Agents and Chemotherapy, vol. 7, No. 5, May 1975, pp. 500-508.
(Continued)

*Primary Examiner* — Johann R Richter
*Assistant Examiner* — Danielle Sullivan
(74) *Attorney, Agent, or Firm* — Dilworth & Barrese, LLP

(57) ABSTRACT

An antimicrobial mixture comprising or consisting of:
one or more compounds of the formula (I)

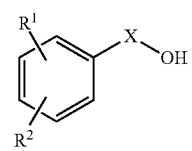

their salts or solvates,
wherein $R^1$ and $R^2$ in each case independently of one another are chosen from the group consisting of: H, OH, F, Cl, Br and I,
and wherein X in each case denotes:

$(CH_2)_m$ where m=1, 2 or 3
or $O{-}(CH_2){-}_n$ where n=1, 2 or 3
or $O{-}CH_2{-}CH(R^3)$ where $R^3=CH_3$ or $CH_2OH$
or $(CH_2{-}O){-}_p CH_2$ where p=1 or 2,
wherein in the compound(s) of the formula I
a primary alcohol function $CH_2OH$ is optionally replaced by a radical which is chosen from the group consisting of $CH_2OR^4$, COOH and $COOR^4$ and/or
a secondary alcohol function CHOH is optionally replaced by the radical $CHOR^4$,
wherein each $R^4$ denotes an aliphatic or aromatic radical, independently of the meaning of further radicals, and
one, two or more compounds chosen from the group consisting of the tropolones of the formula (II)

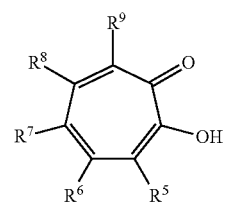

wherein the substituents $R^5, R^6, R^7, R^8, R^9$ independently of one another have the following meaning:
H;
linear or branched, saturated or unsaturated, aliphatic hydrocarbon radical having up to 30 C atoms;
OH;
(Continued)

OR$^{10}$, wherein R$^{10}$ is a linear or branched, saturated or unsaturated, aliphatic hydrocarbon radical having up to 30 C atoms;
COOH;
COOR$^{11}$, wherein R$^{11}$ is a linear or branched, saturated or unsaturated, aliphatic hydrocarbon radical having up to 30 C atoms;
NO$_2$,
NH$_2$,
F, Cl, Br, I.

10 Claims, No Drawings

Related U.S. Application Data

(60) Provisional application No. 60/692,041, filed on Jun. 17, 2005.

(51) Int. Cl.

| | | |
|---|---|---|
| *C07D 495/04* | (2006.01) | |
| *A01N 35/06* | (2006.01) | |
| *A61K 8/35* | (2006.01) | |
| *A61K 31/045* | (2006.01) | |
| *A61K 31/047* | (2006.01) | |
| *A61K 31/05* | (2006.01) | |
| *A61K 31/075* | (2006.01) | |
| *A61K 31/122* | (2006.01) | |
| *A61K 45/06* | (2006.01) | |
| *A61Q 5/12* | (2006.01) | |
| *A61Q 17/00* | (2006.01) | |
| *A61Q 17/04* | (2006.01) | |
| *A61Q 19/00* | (2006.01) | |
| *A01N 43/90* | (2006.01) | |
| *A61Q 5/02* | (2006.01) | |
| *A61Q 15/00* | (2006.01) | |
| *A61Q 19/08* | (2006.01) | |

(52) U.S. Cl.
CPC .......... *A61K 31/045* (2013.01); *A61K 31/047* (2013.01); *A61K 31/05* (2013.01); *A61K 31/075* (2013.01); *A61K 31/122* (2013.01); *A61K 45/06* (2013.01); *A61Q 5/12* (2013.01); *A61Q 17/005* (2013.01); *A61Q 17/04* (2013.01); *A61Q 19/00* (2013.01); *C07D 495/04* (2013.01); *A01N 43/90* (2013.01); *A61K 2800/52* (2013.01); *A61K 2800/524* (2013.01); *A61K 2800/59* (2013.01); *A61Q 5/02* (2013.01); *A61Q 15/00* (2013.01); *A61Q 17/00* (2013.01); *A61Q 19/005* (2013.01); *A61Q 19/007* (2013.01); *A61Q 19/08* (2013.01)

(58) Field of Classification Search
USPC ......................................................... 504/246
See application file for complete search history.

(56) References Cited

U.S. PATENT DOCUMENTS

| | | | | |
|---|---|---|---|---|
| 4,990,330 | A | * | 2/1991 | Oyama .......................... 424/59 |
| 6,554,620 | B1 | * | 4/2003 | Iwai ............................ 424/439 |
| 8,647,651 | B2 | | 2/2014 | Schmaus et al. |

FOREIGN PATENT DOCUMENTS

| | | | | |
|---|---|---|---|---|
| JP | 02243607 | * | 9/1990 | ............ A01N 37/10 |
| JP | 2003-012420 A | | 1/2003 | |
| JP | 2003-335621 A | | 11/2003 | |
| JP | 2005-162636 A | | 6/2005 | |
| WO | 99/45771 A | | 9/1999 | |
| WO | 01/99376 A2 | | 12/2001 | |
| WO | 03/030813 A2 | | 4/2003 | |
| WO | 2006/082151 A | | 8/2006 | |

OTHER PUBLICATIONS

Pillai et al, "Cosmetic compositions containing mixtures of alkane diols and one or more compounds selected from chelating agents, tropolone compounds and sesquiterpanes," Research Disclosure, Mason Publications, Hampshire, GB, vol. 491, No. 22, Mar. 2005.

* cited by examiner

SYNERGISTIC MIXTURES OF AROMATIC ALCOHOLS AND DERIVATIVES THEREOF AND TROPOLONE (DERIVATIVES)

CROSS REFERENCE TO RELATED APPLICATIONS

This application is a continuation-in-part of co-pending PCT/EP2006/063264, filed on Jun. 16, 2006, and based upon U.S.S.N. 60/692,041 filed on Jun. 17, 2005 under the International Convention.

FIELD OF THE INVENTION

The present invention relates to the field of antimicrobial active compounds, and in particular certain mixtures, formulations and foodstuffs comprising certain compounds (alcohols, ethers, esters, acids, corresponding salts and solvates) of a formula (I) (in this context, see below) and at least one tropolone (derivative) of the formula (II) (in this context, see below) and to products comprising such mixtures in an antimicrobially active amount.

The invention also relates to certain uses and processes in which the mixtures according to the invention are employed.

RELATED ART OF THE INVENTION

In the cosmetics and pharmaceutical and in the foodstuffs industry there is a constant need for agents having antimicrobial properties, in particular for the preservation of products which are otherwise perishable (such as e.g. cosmetics, pharmaceutical products or foodstuffs), but also for direct cosmetic or therapeutic treatment of microorganisms which can have an adverse influence on the human or animal body. Reference may be made by way of example to microorganisms which can cause body odour, acne, mycoses or the like.

In the technical fields referred to a large number of antimicrobial active compounds are indeed already employed, but alternatives nevertheless continue to be sought, in order to be able to perform targeted specific treatments and/or reduce side effects. In this context, however, in the search for alternative agents having an antimicrobial and in particular preserving action it is to be noted that the substances used in the cosmetics, pharmaceutical and/or foodstuffs field must be

- toxicologically acceptable,
- readily tolerated by the skin,
- stable (in particular in the conventional cosmetic and/or pharmaceutical formulations),
- largely and preferably completely odourless and
- inexpensive to prepare (i.e. employing standard processes and/or starting from standard precursors).

The search for suitable (active) substances which have one or more of the properties mentioned to an adequate extent is made difficult for the person skilled in the art in that there is no clear dependency between the chemical structure of a substance on the one hand and its biological activity against certain microorganisms (germs) and its stability on the other hand. Furthermore, there is no predictable connection between the antimicrobial action, the toxicological acceptability, the skin tolerability and the stability of a substance.

SUMMARY OF THE INVENTION

According to a first aspect, the present invention relates to an antimicrobial mixture comprising or consisting of:

(a) one or more compounds of the formula (I)

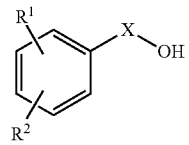

I their salts or solvates,
wherein $R^1$ and $R^2$ in each case independently of one another are chosen from the group consisting of: H, OH, F, Cl, Br and I,
and wherein X in each case denotes:

where m=1, 2 or 3
or

where n=1, 2 or 3
or

O—CH$_2$—CH(R$^3$)

where $R^3$=CH$_3$ or CH$_2$OH

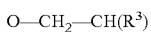

or
where p=1 or 2,
wherein in the compound(s) of the formula I
a primary alcohol function CH$_2$OH is optionally replaced by a radical which is chosen from the group consisting of CH$_2$OR$^4$, COOH and COOR$^4$
and/or
a secondary alcohol function CHOH is optionally replaced by the radical CHOR$^4$,
wherein each $R^4$ denotes an aliphatic or aromatic radical, independently of the meaning of further radicals,
and
one, two or more compounds chosen from the group consisting of the tropolones of the formula (II)

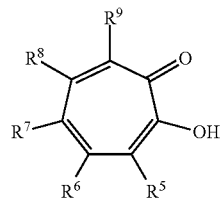

II wherein the substituents $R^5$, $R^6$, $R^7$, $R^8$, $R^9$ independently of one another have the following meaning:
H;
linear or branched, saturated or unsaturated, aliphatic hydrocarbon radical having up to 30 C atoms;
OH;
OR$^{10}$, wherein $R^{10}$ is a linear or branched, saturated or unsaturated, aliphatic hydrocarbon radical having up to 30 C atoms;
COOH;
COOR$^{11}$, wherein $R^{11}$ is a linear or branched, saturated or unsaturated, aliphatic hydrocarbon radical having up to 30 C atoms;

NO$_2$,
NH$_2$,
F, Cl, Br, I.

If X has the meaning (CH$_2$)$_m$, the compounds benzyl alcohol (m=1) and 2-phenylethyl alcohol (m=2) are preferred.

If X has the meaning O—(CH$_2$)$_n$, the compounds 2-phenoxyethanol (n=2) and 3-phenoxypropanol (n=3) are preferred.

If X has the meaning O—CH$_2$—CH(R$^3$), the compounds 1-phenoxy-propan-2-ol (R$^3$=CH$_3$) and 3-phenoxy-propane-1,2-diol (R$^3$=CH$_2$OH) result. The two compounds mentioned are preferred for use in an antimicrobial mixture according to the invention.

If X has the meaning (CH$_2$—O)$_p$CH$_2$, the compounds benzyloxymethanol (p=1) and (benzyloxymethoxy)-methanol (p=2) result. The two compounds are preferred for use in antimicrobial mixtures according to the invention.

The preferred compounds of the formula (I) are shown once again below, the particular structural formulae assigned containing no indications of enantiomers which may be preferred.

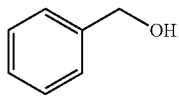

Benzyl alcohol (CARN: 100-51-6)

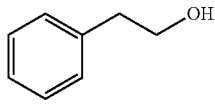

2-phenylethyl alcohol (CARN: 60-12-8),

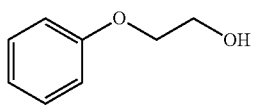

2-Phenoxyethanol (CARN: 122-99-6),

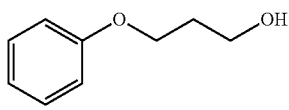 [SMILES: OCCCOc1ccccc1]

3-Phenoxypropanol (CARN: 6180-61-6),

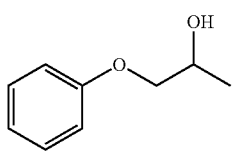

1-Phenoxy-propan-2-ol (CARN: 770-35-4);

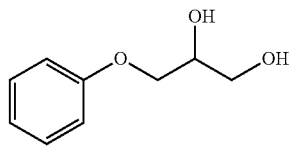 [SMILES: OCC(O)COc1ccccc1]

3-Phenoxy-propane-1,2-diol (CARN: 538-43-2),

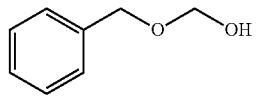

Benzyloxymethanol (CARN: 14548-60-8)

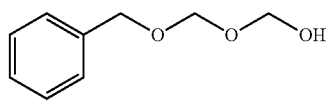 [SMILES: OCOCOCc1ccccc1]

(Benzyloxymethoxy)-methanol (CARN: 35445-70-6).

The use of 2-phenoxyethanol is particularly preferred.

It has already been indicated that instead of the alcohols of the formula I reproduced above by their structural formula, certain derivatives which are derived from the said alcohols by optionally replacing a primary alcohol function CH$_2$OH by a radical which is chosen from the group consisting of CH$_2$OR$^4$, COOH and COOR$^4$ and/or a optionally replacing a secondary alcohol function CHOH by the radical CHOR$^4$, wherein each R$^4$ denotes an aliphatic or aromatic radical, independently of the meaning of further radicals, can be employed in an antimicrobial mixture according to the invention.

This possibility of the (alternative or additional) use of derivatives (ether, carboxylic acid or ester) relates in particular to the eight alcohols characterized above as preferred. Instead of the said alcohols, the corresponding ethers, carboxylic acids or esters can thus also be employed.

Alternatively or additionally, the corresponding salts or solvates of the carboxylic acids can also be employed.

In the functional groups CH$_2$OR$^4$ and COOR$^4$ of the derivatives, R$^4$ preferably denotes a saturated or unsaturated, branched or unbranched radical having 1, 2, 3, 4 or 5 C atoms or an optionally substituted phenyl or benzyl radical.

In the mixtures according to the invention, the constituents (a) and (b) in the mixture are preferably adjusted such that their antimicrobial action is intensified synergistically.

Compounds which are preferred for use as constituent (b) in antimicrobial mixtures according to the invention are:
tropolone (formula (II): R$^5$, R$^6$, R$^7$, R$^1$, R$^9$=H),
alpha-thujaplicin (formula (II): R$^5$=iso-propyl, R$^6$, R$^7$, R$^8$, R$^9$=H),
beta-thujaplicin (formula (II): R$^6$=iso-propyl, R$^5$, R$^7$, R$^8$, R$^9$=H)
gamma-thujaplicin (formula (II): R$^7$=iso-propyl, R$^5$, R$^6$, R$^8$, R$^9$=H)
or a mixture of these compounds.

The structural formula of the compound tropolone (CAS No.: 533-75-5; 2,4,6-cycloheptatrien-1-one, 2-hydroxy), which is particularly preferred for use in a mixture according to the invention, is:

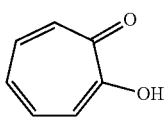

The invention is based on the surprising finding that the mixtures according to the invention show a synergistically intensified antimicrobial effect at least against selected genus, in particular against *Aspergillus niger*, a mould which can be combated only with great difficulty, and also against other germs.

In particular, it has been found that the mixtures according to the invention can be used outstandingly as an antimicrobial active compound mixture, in particular for preserving otherwise perishable articles (see above).

Although persons skilled in the art have already addressed the antimicrobial properties of aromatic alcohols, such as e.g. benzyl alcohol, 2-phenylethyl alcohol, 2-phenoxyethanol, 3-phenoxypropanol, 1-phenoxy-propan-2-ol, 3-phenoxy-propane-1,2-diol, benzyloxymethanol and (benzyloxymethoxy)-methanol, and of tropolone and tropolone derivatives extensively, there has hitherto been no indication that the mixtures according to the invention of such compounds have a significantly improved antimicrobial action (at least against selected germs) in the individual case.

The antimicrobial action of tropolone and tropolone derivatives is known e.g. from Antimicrob. Agents Chemother. vol. 7(5), 500-506 (1975). However, studies of a synergistically intensified activity against *Aspergillus niger* of a combination of tropolone with the aromatic alcohols, acids, their salts and solvates and ester and ethers to be employed according to the invention are not disclosed in any of these publications.

The antimicrobial action of benzyl alcohol, 2-phenoxyethanol and further aromatic alcohols to be employed according to the invention is described in detail e.g. in "Handbuch der Konservierungsmittel [Preservatives Handbook]" (ed.: Fachgruppe Konservierung und Betriebshygiene der Deutschen Gesellschaft für wissenschaftliche und angewandte Kosmetik e.V (DGK); Verlag für chemische Industrie, H. Ziolkowsky GmbH, D-86150 Augsburg; ISBN 3 87846 171 2). However, studies of a synergistically intensified activity against *Aspergillus niger* in combination with tropolone or a tropolone derivative are disclosed neither in this nor in further publications.

The aromatic alcohols to be employed according to the invention usually per se have only a deficient action, for example, against moulds such as *Aspergillus niger*. In respect of individual aromatic alcohols, a gap in the activity on moulds (e.g. the "problem germ" *Aspergillus niger*) is thus to be recorded. High use concentrations of individual aromatic alcohols have therefore hitherto been necessary for complete inhibition of moulds.

It was therefore particularly surprising that the mixtures according to the invention show a highly synergistic activity, and in the treatment of *Aspergillus niger* are significantly superior to:

individually dosed tropolones or tropolone derivatives of the formula (II) and mixtures of tropolone (derivatives) of the formula (II) or individually dosed compounds of the formula (I), in particular individually dosed aromatic alcohols, such as e.g. benzyl alcohol, 2-phenylethyl alcohol, 2-phenoxyethanol, 3-phenoxypropanol, 1-phenoxy-propan-2-ol, 3-phenoxy-propane-1,2-diol, benzyloxymethanol and (benzyloxymethoxy)-methanol and mixtures of these compounds at the same concentration, in particular in respect of the reduction in germ count and the speed of the reduction in germ count.

On the basis of the particularly significant intensification in the action of their constituents, mixtures according to the invention are suitable in particular for combating *Aspergillus niger* even at a low dosage of the mixture according to the invention.

For the preparation of effective mixtures according to the invention which cause a particularly rapid reduction in the *Aspergillus niger* germ count, it is sufficient to mix one mixture constituent (a), such as benzyl alcohol, 2-phenylethyl alcohol, 2-phenoxyethanol, 3-phenoxypropanol, 1-phenoxy-propan-2-ol, 3-phenoxy-propane-1,2-diol, benzyloxymethanol and/or (benzyloxymethoxy)methanol, with a small amount of constituent (b), i.e. one, two or more tropolones of the formula (II), for example an amount of (b) in the range of 0.001-10 wt. %, preferably only 0.5-4 wt. %, based on the amount of constituent (a). If an amount of 0.5 wt. % e.g. of 2-phenoxyethanol is employed, this corresponds e.g. to an amount of tropolone(s) of just about 0.005 wt. %, in each case based on the total weight of the end product.

Based on the total weight of constituents (a) and (b) to be employed according to the invention, the content of constituent (a) is preferably in the range of from 80 to 99.99 wt. %, but preferably in the range of 94-99.5 wt. %.

The antimicrobial mixtures according to the invention are suitable for preservation and antimicrobial treatment of perishable products, such as e.g. cosmetic products, pharmaceutical products or foods (foodstuffs).

A cosmetic or pharmaceutical formulation according to the invention or a foodstuff according to the invention comprises:

a mixture which is antimicrobial according to the invention and comprises or consists of constituents (a) and (b) as stated above and further conventional constituents, the total amount of constituents (a) and (b) being in the range of from 0.01 to 10 wt. %, based on the total weight of the formulation or of the foodstuff.

For the preparation of such a formulation or such a foodstuff, the corresponding (conventionally otherwise perishable) product is brought into contact with an antimicrobially active amount, preferably an amount which is active against *Aspergillus niger*, of an antimicrobial mixture according to the invention.

On the basis of their synergistically intensified antimicrobial activity, however, the mixtures according to the invention can also be employed (a) for the cosmetic treatment of microorganisms which cause body odour, (b) for the cosmetic treatment of microorganisms which cause acne, (c) for the cosmetic treatment of microorganisms which cause mycoses and (d) for the treatment of microorganisms on or in inanimate matter.

On the basis of the synergistic action of constituents (a) and (b) in an antimicrobial mixture or formulation according to the invention or a corresponding foodstuff, an adequate antimicrobial activity can already be achieved if the amount of constituent (a) and/or the amount of constituent (b) in each case considered in itself is not antimicrobially active. However, the total amount of constituents (a) and (b) is then antimicrobially active.

The present invention also relates to the use of an antimicrobial mixture according to the invention as an antimicrobial active compound mixture. In this context, that stated above applies accordingly in respect of the compounds of constituents (a) and (b) which are preferably to be employed.

The mixtures according to the invention display their synergistically intensified antimicrobial action against a large number of Gram-positive bacteria, Gram-negative bacteria, moulds and yeasts, which in particular renders possible preservation and antimicrobial treatment of a large number of cosmetic formulations. A particularly good action exists against Gram-negative bacteria, such as *Escherichia coli* and *Pseudomonas aeruginosa*, against yeasts, such as *Candida albicans*, and precisely—as already mentioned—against fungi, such as *Aspergillus niger*. The very good activity of the mixtures according to the invention against *Aspergillus niger*, a mould which can be combated only with great difficulty, is to be regarded as particularly advantageous here.

The present invention furthermore relates to corresponding methods for the cosmetic and/or therapeutic treatment of germs, in particular on the human body, and in particular especially of (i) microorganisms which cause body odour, (ii) microorganisms which cause acne and/or (iii) microorganisms which cause mycoses, comprising topical application of an antimicrobially active amount of a mixture according to the invention. The contents of the said constituents (a) and (b) of the mixtures are therefore preferably adjusted such that their antimicrobial action is intensified synergistically.

Preferred embodiments of the methods according to the invention correspond to the preferred embodiments of the use according to the invention which are explained above.

The human skin is populated by a large number of various microorganisms, which include the microorganisms already mentioned above, as well as others. Most of these microorganisms are not pathogenic and are irrelevant to the physiological state of the skin and to the odour thereof. On the other hand, others can influence the healthy state of the skin decisively.

As our own studies have now shown, the synergistically active mixtures according to the invention have a good action against *Staphylococcus epidermidis, Corynebacterium xerosis, Brevibacterium epidermidis, Propionibacterium acnes* and against *Trichophyton* and *Epidermophyton* species, so that they can be employed as agents for the treatment of (combating) underarm and foot odour or body odour generally, as agents for combating acne, as antidandruff agents and for the treatment of mycoses (in particular dermatomycoses).

In the context of the present text, "treatment" is understood here as meaning any form of influencing of the microorganisms in question in which the multiplication of these microorganisms is inhibited and/or the microorganisms are killed.

The use concentration of a mixture according to the invention (which is preferably in a preferred embodiment) when used as a preservative or antimicrobial active compound in a foodstuff or a cosmetic or pharmaceutical formulation is preferably in the range of from 0.01 to 10 wt. %, but particularly preferably in the range of from 0.05 to 5 wt. %, in each case based on the total weight of the foodstuff or the formulation. The foodstuff and formulation additionally comprise conventional further constituents, in this context see below. The particular content of constituents (a) and/or (b) to be used according to the invention in mixtures according to the invention can be below the amount regarded as antimicrobially active in itself if the total amount of these substances which is present is sufficiently high to achieve an antimicrobial action of the total mixture. This applies in particular to the action against *Aspergillus niger*.

In a preferred method according to the invention for the cosmetic and/or therapeutic treatment of (i) microorganisms which cause body odour, (ii) microorganisms which cause acne and/or (iii) microorganisms which cause mycoses, the use concentration of the synergistically active mixtures according to the invention is also in the range between 0.01 and 10 wt. %, and particularly preferably in the range between 0.05 and 5 wt. %, in each case based on the total weight of the cosmetic or pharmaceutical product which comprises the mixture.

The synergistically active mixtures can be employed here (a) prophylactically or (b) as required.

The concentration of the amount of active compound to be applied e.g. daily varies and depends on the physiological state of the subject and individual-specific parameters, such as age or body weight. The synergistically active mixtures according to the invention can be employed either by themselves or in combination with further antimicrobially active substances.

Further uses/methods and mixtures/compositions according to the invention can be found in the following statements and the attached patent claims.

Compositions which comprise a mixture according to the invention are, especially if they are employed against germs which cause body odour, as a rule applied topically in the form of solutions, creams, lotions, gels, sprays or the like. For other purposes, an oral (tablets, capsules, powders, drops), intravenous, intraocular, intraperitoneal or intramuscular administration or an administration in the form of an impregnated dressing is appropriate in some cases.

The mixtures according to the invention can be incorporated without difficulties into the usual cosmetic and/or dermatological formulations, such as, inter alia, pump sprays, aerosol sprays, creams, ointments, tinctures, lotions, nail care products (e.g. nail varnishes, nail varnish removers, nail balsams) and the like. It is also possible here, and in some cases advantageous, to combine the synergistic mixtures according to the invention with further active compounds, for example with other antimicrobially, antimycotically or antivirally active substances. The cosmetic and/or dermatological/keratological formulations comprising the synergistic mixtures according to the invention can otherwise have the conventional composition here and serve for the treatment of skin and/or hair in the sense of a dermatological treatment or a treatment in the sense of care cosmetics. However, they can also be employed in make-up products in decorative cosmetics.

If the mixtures according to the invention are employed as active compounds for preserving organic material, one or more further preservatives can advantageously additionally be employed as constituent(s) (c). Preservatives which are preferably chosen here are those such as 2,4-hexadienoic acid (sorbic acid) and its salts, formaldehyde and paraformaldehyde, 2-hydroxybiphenyl ether and its salts, 2-zinc-sulfidopyridine N-oxide, inorganic sulfites and bisulfites, sodium iodate, chlorobutanolum, 4-ethylmercury-(II)5-amino-1,3-bis(2-hydroxybenzoic acid), its salts and esters, dehydracetic acid, formic acid, 1,6-bis(4-amidino-2-bromophenoxy)-n-hexane and its salts, the sodium salt of ethylmercury-(II)-thiosalicylic acid, phenylmercury and its salts, 10-undecylenic acid and its salts, 5-amino-1,3-bis(2-ethylhexyl)-5-methyl-hexahydropyrimidine, 5-bromo-5-nitro-1,3-dioxane, 2-bromo-2-nitro-1,3-propanediol, N-(4-chlorophenyl)-N'-(3,4-dichlorophenyl)-urea, 4-chloro-m-cresol, 2,4,4'-trichloro-2'-hydroxy-diphenyl ether, 4-chloro-3,5-dimethylphenol, 1,1'-methylene-bis(3-(1-hydroxymethyl-2,4-dioximidazolidin-5-yl)urea), poly (hexamethylenediguanide) hydrochloride, hexamethylenetetramine, 1-(3-chloroallyl)-3,5,7-triaza-1-azonia-adamantane chloride, 1-(4-chlorophenoxy)-1-(1H-imidazol-1-yl)-3,3-dimethyl-2-butanone, 1,3-bis-(hydroxymethyl)-5,5-dimethyl-2,4-imidazolidinedione, Octopirox, 1,2-dibromo-2,4-dicyanobutane, benzethonium chloride, 2,2'-methylene-bis(6-bromo-4-chlorophenol), bromochlorophene, mixture of 5-chloro-2-methyl-3(2H)-isothiazolinone and 2-methyl-3(2H)-isothiazolinone with magnesium chloride and magnesium nitrate, 2-benzyl-4-chlorophenol, 3-(4-Chlorphenoxy)-1,2-propanediol (Chlorphenesin), 2-chloroacetamide, chlorhexidine, chlorhexidine acetate, chlorhexidine gluconate, chlorhexidine hydrochloride, N-alkyl($C_{12}$-$C_{22}$)trimethyl-ammonium bromide and chloride, 4,4-dimethyl-1,3-oxazolidine, N-hydroxymethyl-N-(1,3-di(hydroxymethyl)-2,5-dioxoimidazolidin-4-yl)-N'-hydroxy-methylurea, 1,6-bis(4-amidinophenoxy)-n-hexane and its salts, glutaraldehyde, 5-ethyl-1-aza-3,7-dioxabicyclo(3.3.0)octane, 3-(4-chlorophenoxy)-1,2-propanediol, hyamines, alkyl-($C_8$-$C_{18}$)-dimethyl-benzyl-ammonium chloride, alkyl-($C_8$-$C_{18}$)-dimethyl-benzylammonium bromide, alkyl-($C_8$-$C_{18}$)-dimethyl-benzylammonium saccharinate, benzyl hemiformal, 3-iodo-2-propynyl butylcarbamate, sodium hydroxymethyl-aminoacetate or sodium hydroxymethyl-aminoacetate, imidazolidinylurea, diazolidinylurea, sodium hydroxymethylglycinate, chlorphenesin, DMDM hydantoin, methylchloroisothiazolinone and methylisothiazolinones as well as certain 1,2-alkanediols.

Combinations with one or more branched or unbranched 1,2-alkanediols having 6 to 12 carbon atoms are preferred in particular. Particularly preferred combinations are those with:
    1,2-hexanediol or
    1,2-octanediol or
    1,2-decanediol or
    a mixture of 1,2-hexanediol and 1,2-octanediol or
    a mixture of 1,2-hexanediol and 1,2-decanediol or
    a mixture of 1,2-octanediol and 1,2-decanediol or
    a mixture of 1,2-hexanediol, 1,2-octanediol and 1,2-decanediol.

Such mixtures which, in addition to constituents (a) and (b), also comprise one or more of the diols mentioned, often have an activity which is particularly intensified synergistically.

If the mixtures according to the invention are to be employed chiefly for inhibition of the growth of undesirable microorganisms on or in animal organisms, a combination with one or more further antibacterial or antimycotic active substances (as additional constituent(s) (c)is also advantageous here in some cases. In this respect, further active compounds which are worth mentioning, in addition to the large group of conventional antibiotics, are, in particular, the products relevant for cosmetics, such as (triclosan, climbazole, octoxyglycerol (ethylhexyl glycerol, Sensiva SC50), Octopirox (1-hydroxy-4-methyl-6-(2,4,4-trimethylpentyl)-2(1H)pyridone, 2-aminoethanol), chitosan, totarol, farnesol, geranylacetol, glycerol monolaurate, arylalkyl alcohols, such as e.g. 4-methyl-4-phenyl-2-pentanols (DE 101 43 434, in particular 4-methyl-4-phenyl-2-pentanol), muguet alcohol (2,2-dimethyl-3-phenylpropanol), other arylalkyl alcohols (e.g. as disclosed in DE 44 47 361, DE 103 30 697, U.S. Pat. No. 4,110,430 or EP 1 157 687), essential oils with antimicrobial properties and isolates from essential oils with antimicrobial properties like e.g. thymol or eugenol, perfume oils or single aroma chemicals with antimicrobial activity, polyglycerol esters, such as e.g. polyglyceryl 3-caprylates, or combinations of the substances mentioned, which are employed, inter alia, against underarm odour, foot odour or dandruff formation.

The mixtures according to the invention can advantageously be combined, in particular in cosmetic formulations, with further conventional constituents, such as, for example:

Further preservatives, further antimicrobial agents, such as e.g. further antibacterial agents or fungicides, abrasives, antiacne agents, agents against ageing of the skin, anticellulitis agents, antidandruff agents, antiinflammatory agents, irritation-preventing agents, irritation-inhibiting agents, antioxidants, astringents, perspiration-inhibiting agents, antiseptic agents, antistatics, binders, buffers, carrier materials, chelating agents, cell stimulants, cleansing agents, care agents, depilatory agents, surface-active substances, deodorizing agents, antiperspirants, softeners, emulsifiers, enzymes, essential oils, fibres, film-forming agents, fixatives, foam-forming agents, foam stabilizers, substances for preventing foaming, foam boosters, gelling agents, gel-forming agents, hair care agents, hair-setting agents, hair-straightening agents, moisture-donating agents, moisturizing substances, moisture-retaining substances, bleaching agents, strengthening agents, stain-removing agents, optically brightening agents, impregnating agents, dirt-repellent agents, friction-reducing agents, lubricants, moisturizing creams, ointments, opacifying agents, plasticizing agents, covering agents, polish, gloss agents, polymers, powders, proteins, re-oiling agents, abrading agents, silicones, skin-soothing agents, skin-cleansing agents, skin care agents, skin-healing agents, skin-lightening agents, skin-protecting agents, skin-softening agents, cooling agents, skin-cooling agents, warming agents, skin-warming agents, stabilizers, UV-absorbing agents, UV filters, detergents, fabric conditioning agents, suspending agents, skin-tanning agents, thickeners, vitamins, oils, waxes, fats, phospholipids, saturated fatty acids, mono- or polyunsaturated fatty acids, α-hydroxy acids, polyhydroxy-fatty acids, liquefiers, dyestuffs, colour-protecting agents, pigments, anticorrosives, aromas, flavouring substances, odoriferous substances, polyols, surfactants, electrolytes, organic solvents or silicone derivatives.

The mixtures according to the invention can moreover also particularly advantageously be employed in combination with perspiration-inhibiting active compounds (antiperspirants) for combating body odour. Perspiration-inhibiting active compounds which are employed are, above all, aluminium salts, such as aluminium chloride, aluminium hydrochloride, nitrate, sulfate, acetate etc. In addition, however, the use of compounds of zinc, magnesium and zirconium may also be advantageous. For use in cosmetic and dermatological antiperspirants, the aluminium salts and—to a somewhat lesser extent—aluminium/zirconium salt combinations have essentially proved suitable. The aluminium hydroxychlorides which are partly neutralized and therefore tolerated better by the skin, but not quite so active, are additionally worth mentioning.

If the mixtures according to the invention are to be employed for antimicrobial treatment of a surface (e.g. of a human or animal body), a combination with (metal) chelators is advantageous in some cases. (Metal) chelators which are preferably to be employed here are, inter alia, α-hydroxy fatty acids, phytic acid, lactoferrin, α-hydroxy acids, such as, inter alia, citric acid, ascorbic acid, lactic acid and malic acid, and humic acids, bile acids, bile extracts, bilirubin, biliverdin or EDTA, EGTA and derivatives thereof.

For use, the cosmetic and/or dermatologically active mixtures according to the invention are applied to the skin and/or hair in a sufficient amount in the conventional manner for cosmetics and dermatics. In this context, cosmetic and dermatological formulations which comprise a mixture according to the invention and additionally act as sunscreen compositions offer particular advantages. These formulations advantageously comprise at least one UVA filter and/or at least one UVB filter and/or at least one inorganic pigment. In this context, the formulations can be in various forms such as are conventionally employed e.g. for sunscreen formulations. They can thus be e.g. a solution, an emulsion of the water-in-oil (W/O) type or of the oil-in-water (O/W) type or a multiple emulsion, for example of the water-in-oil-in-water (W/O/W) type, a gel, a hydrodispersion, a solid stick or also an aerosol.

As mentioned, formulations which comprise a mixture according to the invention can advantageously be combined with substances which absorb UV radiation, the total amount of the filter substances being e.g. 0.01 wt. % to 40 wt. %, preferably 0.1% to 10 wt. %, in particular 1.0 to 5.0 wt. %, based on the total weight of the formulations, in order to provide cosmetic formulations which protect the hair or skin from ultraviolet radiation.

It is known in the art that preserving aqueous sunscreen formulations containing a relatively high amount of organic U filters (and mostly a relatively high sun protection factor (SPF), typically a SPF of about 15 and higher) is very difficult, especially against yeasts, in particular *Candida* yeasts (cf. U.S. Pat. No. 5,292,529). Hitherto it is not quite understood why such sunscreen formulations have these preserving problems.

It has now been found that the mixtures according to the invention, in particular mixtures comprising tropolone, preferably in combination with phenoxyethanol, have an excellent antimicrobial activity against yeasts, in particular against *Candida albicans*.

Preferred sunscreen formulations according to the present invention are aqueous emulsions, preferably of the water-in-oil (W/O) or of the oil-in-water (O/W) type or a multiple emulsion, for example of the water-in-oil-in-water (W/O/W) type, more preferably of the oil-in-water (O/W) type.

Preferred high SPF sunscreen formulations according to the present invention comprise a total amount of organic UV filters of greater than 10 wt. %, preferably in the range of from 12 to 40 wt. %, more preferred in the range of from 15 to 35 wt. %, based on the total weight of the sunscreen formulation.

In this context advantageous organic UV filters are:
p-aminobenzoic acid
p-aminobenzoic acid ethyl ester (25 mol) ethoxylated
p-dimethylaminobenzoic acid-2-ethylhexyl ester
p-aminobenzoic acid ethyl ester (2 mol) N-propoxylated
p-aminobenzoic acid glycerol ester
salicylic acid homomenthyl ester (homosalates) (Neo Heliopan®HMS)
salicylic acid-2-ethylhexyl ester (Neo Heliopan®OS)
triethanolamine salicylate
4-isopropyl benzyl salicylate
anthranilic acid menthyl ester (Neo Heliopan®MA) -(p-carbo-2'-ethylhexyl-1'-oxy)-1,3,5-triazine
phenylene bis-benzimidazyl tetrasulfonic acid disodium salt (Neo Heli
diisopropyl cinnamic acid ethyl ester
p-methoxycinnamic acid-2-ethylhexyl ester (Neo Heliopan®AV)
diisopropyl cinnamic acid methyl ester
p-methoxycinnamic acid isoamyl ester (Neo Heliopan®E 1000)
p-methoxycinnamic acid diethanolamine salt
p-methoxycinnamic acid isopropyl ester
2-ethylhexyl-2-cyano-3,3-diphenyl acrylate (Neo Heliopan®303)
ethyl-2-cyano-3,3'-diphenyl acrylate
2-phenylbenzimidazole sulfonic acid and salts (Neo Heliopan®Hydro)
3-(4'-trimethylammonium)benzylidene bornan-2-one methyl sulfate
terephthalylidene dibornane sulfonic acid and salts (Mexoryl®SX)
4-t-butyl-4'-methoxydibenzoyl methane (avobenzone)/ (Neo Heliopan®357)
β-imidazole-4(5)-acrylic acid (urocanic acid)
2-hydroxy-4-methoxybenzophenone (Neo Heliopan®BB)
2-hydroxy-4-methoxybenzophenone-5-sulfonic acid
dihydroxy-4-methoxybenzophenone
2,4-dihydroxybenzophenone
tetrahydroxybenzophenone
2,2'-dihydroxy-4,4'-dimethoxybenzophenone
2-hydroxy-4-n-octoxybenzophenone
2-hydroxy-4-methoxy-4'-methyl benzophenone
3-(4'-sulfo)benzylidene bornan-2-one and salts
3-(4'-methyl benzylidene)-d,l-camphor (Neo Heliopan®MBC)
3-benzylidene-d,l-camphor
4-isopropyl dibenzoyl methane
2,4,6-trianilino opan®AP)
2,2'-(1,4-phenylene)-bis-(1H-benzimidazole-4,6-disulfonic acid), monosodium salt
N-[(2 and 4)-[2-(oxoborn-3-ylidene)methyl]benzyl]acrylamide polymer
phenol, -(2H-benzotriazol-2-yl)-4-methyl-6-(2-methyl-3 (1,3,3,3-tetramethyl-1-(trimethylsilyl)oxy)disiloxanyl)propyl), (Mexoryl®XL)
4,4'-[(6-[4-(1,1-dimethyl)aminocarbonyl)phenylamino]-1,3,5-triazine-2,4-diyl)diimino]-bis-(benzoic acid-2-ethylhexyl ester) (Uvasorb®HEB)
2,2'-methylene bis-(6-(2H-benzotriazol-2-yl)-4-1,1,3,3-tetramethylbutyl)phenol), (Tinosorb®M)
2,4-bis-[4-(2-ethylhexyloxy)-2-hydroxyphenyl]-1,3,5-triazine
benzylidene malonate polysiloxane (Parsol®SLX)
glyceryl ethylhexanoate dimethoxycinnamate
disodium-2,2'-dihydroxy-4,4'-dimethoxy-5,5'-disulfobenzophenone
dipropylene glycol salicylate
sodium hydroxymethoxybenzophenone sulfonate
4,4',4-(11,3,5-triazine-2,4,6-triyltriimino)-tris-benzoic acid tris(2-ethylhexyl ester) (Uvinul®T150)
2,4-bis-[{(4-(2-ethylhexyloxy)-2-hydroxy}phenyl]-6-(4-methoxyphenyl)-1,3,5-triazine (Tinosorb®S)
2,4-bis-[{(4-(3-sulfonato)-2-hydroxypropyloxy)-2-hydroxy}phenyl]-6-(4-methoxyphenyl)-1,3,5-triazine sodium salt
2,4-bis-[{(3-(2-propyloxy)-2-hydroxypropyloxy)-2-hydroxy}phenyl]-6-(4-methoxyphenyl)-1,3,5-triazine
2,4-bis-[{4-(2-ethylhexyloxy)-2-hydroxy}phenyl]-6-[4-(2-methoxyethyl carbonyl)phenylamino]-1,3,5-triazine 2,4-bis-[{4-(3-(2-propyloxy)-2-hydroxypropyloxy)-2-hydroxy}phenyl]-6-[4-(2-ethylcarboxyl)phenylamino]-1,3,5-triazine
2,4-bis-[{4-(2-ethylhexyloxy)-2-hydroxy}phenyl]-6-(1-methylpyrrol-2-yl)-1,3,5-triazine
2,4-bis-[{4-tris-(trimethylsiloxysilylpropyloxy)-2-hydroxy}phenyl]-6-(4-methoxyphenyl)-1,3,5-triazine
2,4-bis-[{4-(2"-methylpropenyloxy)-2-hydroxy}phenyl]-6-(4-methoxyphenyl)-1,3,5-triazine
2,4-bis-[{4-(1',1',1',3'5',5,5'-heptamethylsiloxy-2"-methylpropyloxy)-2-hydroxy}phenyl]-6-(4-methoxyphenyl)-1,3,5-triazine
2-(4-diethylamino-2-hydroxybenzoyl)benzoic acid hexyl ester (Uvinul® A Plus)
indanylidene compounds in accordance with DE 100 55 940 (=WO 02/38537)

Organic UV filters which are particularly preferred in a sunscreen formulation of the present invention, preferably in an above mentioned (preferred) amount, are:
p-aminobenzoic acid
3-(4'-trimethylammonium)benzylidene bornan-2-one methyl sulfate
salicylic acid homomenthyl ester (Neo Heliopan®HMS)
2-hydroxy-4-methoxybenzophenone (Neo Heliopan®BB)
2-phenylbenzimidazole sulfonic acid (Neo Heliopan®Hydro)
terephthalylidene dibornane sulfonic acid and salts (Mexoryl®SX)
4-tert-butyl-4'-methoxydibenzoyl methane (Neo Heliopan®357)
3-(4'-sulfo)benzylidene bornan-2-one and salts
2-ethylhexyl-2-cyano-3,3-diphenyl acrylate (Neo Heliopan®303)
N-[(2 and 4)-[2-(oxoborn-3-ylidene) methyl]benzyl]acrylamide polymer
p-methoxycinnamic acid-2-ethylhexyl ester (Neo Heliopan®AV)
p-aminobenzoic acid ethyl ester (25 mol) ethoxylated
p-methoxycinnamic acid isoamyl ester (Neo Heliopan®E1000)
2,4,6-trianilino-(p-carbo-2'-ethylhexyl-1'-oxy)-1,3,5-triazine (Uvinul®T150)
phenol, 2-(2H-benzotriazol-2-yl)-4-methyl-6-(2-methyl-3(1,3,3,3-tetramethyl-1-(trimethylsilyl)oxy)disiloxanyl)propyl), (Mexoryl®XL)
4,4'-[(6-[4-(1,1-dimethyl)aminocarbonyl)phenylamino]-1,3,5-triazine-2,4-diyl)diimino]-bis-(benzoic acid-2-ethylhexyl ester) (Uvasorb HEB)
3-(4'-methyl benzylidene)-d,l-camphor (Neo Heliopan®MBC)
3-benzylidene camphor
salicylic acid-2-ethylhexyl ester (Neo Heliopan®OS)
4-dimethylaminobenzoic acid-2-ethylhexyl ester (Padimate O)
hydroxy-4-methoxybenzophenone-5-sulfonic acid and Na salt
2,2'-methylenebis-(6-(2H-benzotriazol-2-yl)-4-1,1,3,3-tetramethylbutyl)phenol) (Tinosorb®M)
phenylene bis-benzimidazyl tetrasulfonic acid disodium salt (Neo Heliopan®AP)
2,4-bis-[{(4-(2-ethylhexyloxy)-2-hydroxy}phenyl]-6-(4-methoxyphenyl)-1,3,5-triazine, (Tinosorb®S)
benzylidene malonate polysiloxane (Parsol®SLX)
menthyl anthranilate (Neo Heliopan®MA)
2-(4-diethylamino-2-hydroxybenzoyl)benzoic acid hexyl ester (Uvinul® A Plus)
indanylidene compounds in accordance with DE 100 55 940 (=WO 02/38537)

Preferred sunscreen formulations according to the present invention have a SPF (sun protection factor) of equal or greater than 15, preferably of equal or greater than 20, more preferably of equal or greater than 30.

Preferred sunscreen formulations according to the present invention comprise 4-(1,1-dimethylethyl)-4'-methoxydibenzoylmethane (4-t-butyl-4'-methoxydibenzoyl methane; avobenzone), preferably in an amount in the range of from 0.2-10 wt. %, more preferred in the range of from 0.5-5 wt. %, based on the total weight of the sunscreen formulation.

In preferred sunscreen formulations according to the present invention the pH-value is in the range of from pH 4 to pH 8, preferably in the range of from pH 4.5 to pH 6.5.

A high content of care substances is regularly advantageous in formulations for topical prophylactic or cosmetic treatment of the skin comprising mixtures according to the invention. According to a preferred embodiment, the compositions comprise one or more animal and/or plant fats and oils having care properties, such as olive oil, sunflower oil, refined soya oil, palm oil, sesame oil, rapeseed oil, almond oil, borage oil, evening primrose oil, coconut oil, shea butter, jojoba oil, sperm oil, beef tallow, neat's foot oil and lard, and optionally further care constituents, such as, for example, fatty alcohols having 8-30 C atoms.

Care substances which can be combined in an outstanding manner with the synergistic mixtures according to the invention moreover also include:
ceramides, where ceramides are understood as meaning N-acylsphingosins (fatty acid amides of sphingosin) or synthetic analogues of such lipids (so-called pseudo-ceramides), which significantly improve the water retention capacity of the stratum corneum.
phospholipids, for example soya lecithin, egg lecithin and cephalins
vaseline, paraffin oils and silicone oils; the latter include, inter alia, dialkyl- and alkylarylsiloxanes, such as dimethylpolysiloxane and methylphenylpolysiloxane, as well as alkoxylated and quaternized derivatives thereof.

Cosmetic formulations which comprise mixtures according to the invention can also comprise antioxidants, it being possible for all the antioxidants which are suitable or usual for cosmetic and/or dermatological uses to be used.

Cosmetic formulations which comprise mixtures according to the invention can also comprise vitamins and vitamin precursors, it being possible for all the vitamins and vitamin precursors which are suitable or usual for cosmetic and/or dermatological uses to be used. There are worth mentioning here, in particular, vitamins and vitamin precursors, such as tocopherols, vitamin A, niacin acid and niacinamide, further vitamins of the B complex, in particular biotin, and vitamin C and panthenol and derivatives thereof, in particular the esters and ethers of panthenol and cationically derivatized panthenols, such as e.g. panthenol triacetate, panthenol monoethyl ether and the monoacetate thereof and cationic panthenol derivatives.

Cosmetic formulations which comprise mixtures according to the invention can also comprise antiinflammatory or redness- or itching-alleviating active compounds. All the antiinflammatory or redness- and itching-alleviating active compounds which are suitable or usual for cosmetic and/or dermatological uses can be used here.

Cosmetic formulations which comprise mixtures according to the invention can also comprise active compounds having a skin-lightening or skin-tanning action. According to the invention, all the skin-lightening or skin-tanning active compounds which are suitable or usual for cosmetic and/or dermatological uses can be used here.

Cosmetic formulations which comprise mixtures according to the invention can also comprise anionic, cationic, nonionic and/or amphoteric surfactants, especially if crystalline or microcrystalline solids, for example inorganic micropigments, are to be incorporated into the formulations.

The invention is explained in more detail in the following with the aid of an example. Unless stated otherwise, the data relate to the weight.

EXAMPLE 1

Comparison of Adequate Preservation of Cosmetic Formulations Comprising 2-phenoxyethanol (Product A, not According to the Invention), Tropolone (Product B, not According to the Invention) and a Mixture of 2-phenoxyethanol and tropolone (Product C, According to the Invention)

Testing for adequate preservation was carried out in accordance with the European Pharmacopoeia.

Testing thus comprises contamination of the formulation, if possible in its final condition, with a prescribed inoculum of suitable microorganisms, storage of the inoculated formulation at a certain temperature, removal of samples from the container at certain intervals of time and determination of the number of microorganisms in the samples removed in this way. The preserving properties are adequate if, under the conditions of the test, a clear reduction or, where appropriate, no increase in the germ count results in the inoculated formulations after the prescribed times at the prescribed temperatures. Experimental details of the test procedure are described in the European Pharmacopoeia (ISBN 3-7692-2768-9; Supplement 2001 to the 3rd Edition, page 421-422, chapter 5.1.3).

Test Germs:

The following microorganism strains were used for the tests for adequate preservation:

A: *Escherichia coli* ATCC 8739

B: *Pseudomonas aeruginosa* ATCC 90270

C: *Staphylococcus aureus* ATCC 6538

D: *Candida albicans* ATCC 10231

E: *Aspergillus niger* ATCC 16404

The initial germ count (CFU/g; "0 value") was in the range of from 220,000 to 280,000 in the various test series.

Formulation:

For the tests for adequate preservation, a defined amount of the active compound combination according to the invention (product C) was incorporated into an O/W emulsion. For comparison purposes, the comparison products (product A and B) were incorporated into separate O/W emulsions.

TABLE 1

Formulations with products A, B and C:

| | INCI name | Manufacturer | Wt. % with "A" | Wt. % with "B" | Wt. % with "C" |
|---|---|---|---|---|---|
| Phase A | | | | | |
| Dracorin CE 614035 | Glyceryl Stearate Citrate | Symrise | 4.0 | 4.0 | 4.0 |
| PCL Solid 660086 | Stearyl Heptanoate, Stearyl Caprylate | Symrise | 3.0 | 3.0 | 3.0 |
| Paraffin oil °E | Paraffinum Liquidum | Parafluid | 7.0 | 7.0 | 7.0 |
| Lanette 18 | Stearyl Alcohol | Cognis | 1.5 | 1.5 | 1.5 |
| Dracorin GMS 647834 | Glyceryl Stearate | Symrise | 1.5 | 1.5 | 1.5 |
| Dow Corning 200 fluid | Dimethicone | Dow Corning | 2.0 | 2.0 | 2.0 |
| Phase B | | | | | |
| Water, demineralized | Water (Aqua) | | to 100 | to 100 | to 100 |
| Carbopol ETD 2050 Polymer | Carbomer | Noveon | 0.15 | 0.15 | 0.15 |
| 2-Phenoxy-ethanol | Phenoxyethanol | Symrise | 1.0 | — | 0.5 |
| Tropolone | | Symrise | — | 0.01 | 0.005 |
| Phase C | | | | | |
| Neutralizer AMP-95 | Amino Methylpropanol | Dow/Angus | 0.1 | 0.1 | 0.1 |
| Total: | | | 100.0 | 100.0 | 100.0 | pH: 5.5

Result:

The results of the preservative stress tests for *Aspergillus niger* for the active compound combinations investigated, comprising the mixture according to the invention (product C) or the comparison systems (products A and B), clearly show a synergistic effect of the mixture according to the invention (product C). In the case of *Aspergillus niger*, a germ which is particularly problematic in respect of preservation of industrial products, it was possible to reduce the germ count to 0 within 7 days by using the mixture according to the invention. By using the mixture according to the invention (product C), it was already possible to reduce the number of colony-forming units from 220,000 to 200 after 2 days (Table 2). In contrast, the active compound contained in product A (2-phenoxyethanol) in a dosage of 1.0 wt. % for comparison purposes rendered possible no such significant reduction in the number of colony-forming units (CFU after 2 days: 113,000) in *Aspergillus niger*, which also applies to product B (tropolone, dosage: 0.01%; CFU after 2 days: 95,000). This test series thus shows by way of example that the active compound mixtures according to the invention have an action which is significantly improved synergistically compared with products A (2-phenoxyethanol) and B (tropolone).

TABLE 2

Testing for adequate preservation for product A (comprising 1% phenoxyethanol), for product B (comprising 0.01% tropolone) and for product C (mixture according to the invention comprising 0.05% phenoxyethanol and 0.005% tropolone).

| | A<br>1%<br>phenoxyethanol | B<br>0.01%<br>tropolone | C<br>0.5%<br>phenoxyethanol<br>and<br>0.005%<br>tropolone |
|---|---|---|---|
| | CFU (colony-forming units) | | |
| | *Aspergillus niger* ATCC 16404 | | |
| 0' count | 220,000 | 220,000 | 220,000 |
| 2 d | 113,000 | 95,000 | 200 |
| 7 d | <100 | <100 | 0 |
| 14 d | 0 | 0 | 0 |
| 28 d | 0 | 0 | 0 |

The calculation of the SI value for treatment of *Aspergillus niger* with a mixture of phenoxyethanol and tropolone after an incubation phase of 2 days is shown below by way of example (Table 3). The calculated SI of 0.0019 clearly shows that the mixture is a highly synergistic combination of active compounds. It was not possible to calculate the 7-day, 14-day and 28-day SI values, since after this incubation phase the germ counts either could not be determined precisely, as in the case of the individual substances (<100), or were 0 (compare Table 1). In these special cases, Kull's equation cannot be used; however, the synergism is also evident for product C in the 7-day values on the basis of the germ count of 0.

TABLE 3

Calculation of the synergy index (SI) at the time 2 days with the aid of the CFU values for product A (phenoxyethanol; dosage: 1%), product B (tropolone; dosage: 0.01%) and for the synergistic mixture according to the invention (ratio of amounts of product A and product B: 1:1; w/w; dosage of phenoxyethanol: 0.5%; dosage of tropolone: 0.005%); test germ: *Aspergillus niger*)

| | A<br>1%<br>phenoxyethanol | B<br>0.01%<br>tropolone | C<br>0.5%<br>phenoxyethanol<br>and<br>0.005%<br>tropolone |
|---|---|---|---|
| *Aspergillus niger*:<br>2 days [CFU/ml]<br>Kull's equation:<br>SI = C × D/A +<br>C × E/B | 113,000 | 95,000 | 200 |
| A: Germ count for substance A | 113,000 | | |
| B: Germ count for substance B | | 95,000 | |
| C: Germ count for mixture A + B | | | 200 |
| D: Content of A in C | | | 0.5 |
| E: Content of B in C | | | 0.5 |
| SI: Synergy index | | | 0.0019 |

Literature: Synergy index:
D. C. Steinberg; Cosmetics & Toiletries 115 (11); p. 59–62 (2000)
F. C. Kull et al.; Applied Microbiology 9; p. 538–541 (1961)

Outstanding results which confirm the superiority of product C according to the invention were likewise obtained in respect of the further test germs.

EXAMPLE 2

Comparison of Adequate Preservation of Cosmetic Formulations with a High Amount of Organic UV Filters and Having a SPF of Equal or Greater than 15

Testing for adequate preservation against germs in sunscreen formulations:

For the tests for adequate preservation, 1 wt. % of the respective active compound were incorporated into separate O/W emulsions: A2 is a comparison formulation and formulation C2 is according to the present invention.

TABLE 4

| Trade Name | INCI | A2 | C2 |
|---|---|---|---|
| Emulsiphos | Potassium cetyl phosphate, hydrogenated palm glycerides | 2.00 | 2.00 |
| PCL Solid | Stearyl heptanoate, stearyl caprylate | 2.00 | 2.00 |
| Lanette 16 | Cetyl alcohol | 1.50 | 1.50 |
| Dragoxat 89 | Ethylhexyl ethylisononanoate | 2.00 | 2.00 |
| Neutral Oil | Caprylic/capric triglyceride | 3.00 | 3.00 |
| Tegosoft TN | C12–15 Alkyl benzoate | 3.00 | 3.00 |
| Neo Heliopan BB | Benzophenone-3 | 6.00 | 6.00 |
| Neo Heliopan HMS | Homosalate | 10.00 | 10.00 |
| Neo Heliopan OS | Ethylhexyl salicylate | 5.00 | 5.00 |
| Neo Heliopan 357 | Butyl methoxy dibenzoylmethane | 3.00 | 3.00 |
| Neo Heliopan AV | Ethylhexyl methoxycinnamate | 7.50 | 7.50 |
| Carbopol ETD 2050 | Carbomer | 0.20 | 0.20 |
| Keltrol T | Xanthan gum | 0.20 | 0.20 |
| Water | Water (Aqua) | 50.45 | 50.45 |
| Glycerol | Glycerine | 3.00 | 3.00 |
| AMP | 2-Amino-2-methyl-1-propanol | 0.15 | 0.15 |

TABLE 4-continued

| Trade Name | INCI | A2 | C2 |
|---|---|---|---|
| Phenonip ® | Phenoxyethanol (and) Methylparaben (and) Butylparaben (and) Ethylparaben (and) Propylparaben | 1.00 | — |
| SPT | Phenoxyethanol, Tropolone | — | 1.00 |

Phenonip ® (not according to the present invention) is a commercially available (Clariant, Nipa preservatives) and in cosmetic formulations widely used antimicrobial active mixture consisting of phenoxyethanol, methylparaben, ethylparaben, butylparaben, propylparaben and isobutylparaben.
SPT is a mixture according to the present invention consisting of 99.0 wt. % phenoxyethanol (2-phenoxyethanol) and 1 wt. % tropolone.

Testing for adequate preservation was carried out in accordance with the European Pharmacopoeia.

Testing thus comprises contamination of the formulation, if possible in its final condition, with a prescribed inoculum of suitable microorganisms, storage of the inoculated formulation at a certain temperature, removal of samples from the container at certain intervals of time and determination of the number of microorganisms in the samples removed in this way. The preserving properties are adequate if, under the conditions of the test, a clear reduction or, where appropriate, no increase in the germ count results in the inoculated formulations after the prescribed times at the prescribed temperatures. Experimental details of the test procedure are described in the European Pharmacopoeia (ISBN 3-7692-2768-9; Supplement 2001 to the 3rd Edition, page 421-422, chapter 5.1.3).

The initial germ count (CFU/g; "0 value") was in the range of from 230,000 to 400,000 in the various test series.

The following two antimicrobial active products were compared in view of their activity and efficacy with respect the above mentioned test germs:
Test Germs:
Preservation test for *Escherichia coli* using strain *Escherichia coli* ATCC 8739

| days | A2 (Phenonip ®) | C2 (SPT) |
|---|---|---|
| 0 | 400,000 | 400,000 |
| 2 | 167,000 | 74,000 |
| 7 | 26,000 | 38,000 |
| 14 | 2,100 | 0 |
| 21 | 0 | 0 |

Preservation test for *Pseudomonas aeruginosa* using strain *Pseudomonas aeruginosa* ATCC 9027

| days | A2 (Phenonip ®) | C2 (SPT) |
|---|---|---|
| 0 | 230,000 | 230,000 |
| 2 | 100 | 0 |
| 7 | 0 | 0 |
| 14 | 0 | 0 |

Preservation test for *Staphylococcus aureus* using strain *Staphylococcus aureus* ATCC 6538

| days | A2 (Phenonip ®) | C2 (SPT) |
|---|---|---|
| 0 | 300,000 | 300,000 |
| 2 | 32,000 | 600 |
| 7 | 900 | 0 |
| 14 | 100 | 0 |
| 21 | 0 | 0 |

Preservation test for *Candida albicans* using strain *Candida albicans* ATCC 10231

| days | A2 (Phenonip ®) | C2 (SPT) |
|---|---|---|
| 0 | 400,000 | 400,000 |
| 2 | 194,000 | 167,000 |
| 7 | 157,000 | 93,000 |
| 14 | 157,000 | 100 |
| 21 | 83,000 | 0 |

Preservation test for *Aspergillus niger* using strain *Aspergillus niger* ATCC 16404

| days | A2 (Phenonip ®) | C2 (SPT) |
|---|---|---|
| 0 | 230,000 | 230,000 |
| 2 | 189,000 | 113,000 |
| 7 | 93,000 | 700 |
| 14 | 93,000 | 0 |
| 21 | 20,000 | 0 |

Formulation examples F1-F16: Cosmetic formulations comprising mixtures of 2-phenoxyethanol and tropolone Some efficiently preserved cosmetic formulations comprising mixtures of 2-phenoxyethanol and tropolone according to the invention are given in the following formulations of Formula 1 to Formula 16.
Formulation F1: Anti-Wrinkle Cream

| Raw Material | % weight |
|---|---|
| Phase 1 | |
| Glyceryl Stearate Citrate | 1.00 |
| Glyceryl Laurate | 1.00 |
| Cetearyl Alcohol | 2.00 |
| Myristyl Myristate | 1.00 |
| Cetearyl Ethylhexanoate | 4.00 |
| Mineral oil | 4.00 |
| Cyclopentasiloxane, Cyclohexasiloxane | 0.50 |
| Acrylates/C10–30 Alkyl Acrylate Crosspolymer | 0.20 |
| Phase 2 | |
| Water | 83.14 |
| Xanthan Gum | 0.10 |
| 1,2-Hexanediol | 1.00 |
| Phase 3 | |
| Sodium Hydroxide 10% solution | 0.10 |
| Phase 4 | |
| *Narcissus Tazetta* Bulb Extract | 1.00 |
| Phase 5 | |
| Phenoxyethanol | 0.80 |
| Tropolone | 0.16 |

Formulation F2: Anti-Inflammatory Lotion

| Raw Material | % weight |
|---|---|
| Phase 1 | |
| Cetearyl Alcohol and Ceteareth-20 | 3.50 |
| Cetearyl Alcohol | 0.50 |
| Stearyl Heptanoate, Stearyl Caprylate | 0.50 |
| Glyceryl Stearate | 1.00 |
| Cetearyl Ethylhexanoate | 4.00 |
| Mineral oil | 3.00 |
| Hydrogenated Coco-Glycerides | 1.00 |

-continued

| Raw Material | % weight |
|---|---|
| Phase 2 | |
| Water | 80.49 |
| Disodium EDTA | 0.10 |
| Xanthan Gum | 0.10 |
| Glycerin | 4.00 |
| Phase 3 | |
| Water, Glycerin, *Avena Sativa* (Oat) Kernel Extract | 1.00 |
| Butylene Glycol, Pentylene Glycol, Dihydroavenanthramide D | 0.10 |
| Phase 4 | |
| Phenoxyethanol | 0.70 |
| Tropolone | 0.01 |

Formulation F3: Sunscreen Lotion

| Raw Material | % weight |
|---|---|
| Phase 1 | |
| Potassium Cetyl Phosphate, Hydrogenated Palm Glycerides | 1.00 |
| Bisabolol | 0.10 |
| Cetearyl Alcohol | 1.50 |
| Myristyl Myristate | 1.00 |
| Cetearyl Ethylhexanoate | 4.00 |
| Stearyl Heptanoate, Stearyl Caprylate | 1.00 |
| Cyclopentasiloxane, Cyclohexasiloxane | 0.50 |
| Butyl Methoxydibenzoylmethane | 1.50 |
| 4-Methylbenzylidene Camphor | 1.50 |
| Ethylhexyl Methoxycinnamate | 7.00 |
| VP/Hexadecene Copolymer | 1.00 |
| Acrylates/C10–30 Alkyl Acrylate Crosspolymer | 0.10 |
| Phase 2 | |
| Water | 75.495 |
| Butylene Glycol | 3.00 |
| Phase 3 | |
| Sodium Hydroxide, 10% solution | 0.50 |
| Phase 4 | |
| Fragrance | 0.20 |
| Phase 5 | |
| Phenoxyethanol | 0.60 |
| Tropolone | 0.005 |

Formulation F4: Anti-Itch Ointment

| Raw Material | % weight |
|---|---|
| Phase 1 | |
| Petrolatum | 60.999 |
| Mineral oil | 30.00 |
| Microcrystalline Wax | 3.00 |
| Beeswax | 5.00 |
| Phase 2 | |
| Zinc acetate | 0.10 |
| Phase 3 | |
| Hydrocortisone butyrate | 0.10 |
| Dihydroavenanthramide E | 0.10 |
| Phase 4 | |
| 1,2-Hexanediol, 1,2-Octanediol (Caprylyl Glycol) | 0.50 |
| Phase 5 | |
| Phenoxyethanol | 0.20 |
| Tropolone | 0.001 |

Formulation F5: Healing Spray

| Raw Material | % weight |
|---|---|
| Phase 1 | |
| Water | 51.69 |
| Ethanol SD40 | 40.00 |
| Disodium EDTA | 0.10 |
| Pentylene Glycol | 4.00 |
| Phase 2 | |
| Polysorbate 20 | 2.00 |
| Phase 3 | |
| Phenoxyethanol | 0.20 |
| Tropolone | 0.01 |
| Phase 4 | |
| Water, Glycerin, Beta-Glucan | 2.00 |

Formulation F6: Soothing Powder

| Raw Material | % weight |
|---|---|
| Phase 1 | |
| Talc | 98.24 |
| Phase 2 | |
| *Eucalyptus* Oil | 0.05 |
| Phase 3 | |
| Zinc oxide | 1.00 |
| Menthol | 0.10 |
| Menthyl Lactate | 0.10 |
| Phase 4 | |
| Lavender oil | 0.109 |
| Phase 5 | |
| Phenoxyethanol | 0.40 |
| Tropolone | 0.001 |

Formulation F7: Moisturising Gel

| Raw Material | % weight |
|---|---|
| Phase 1 | |
| Water | 89.895 |
| Carbomer | 0.60 |
| Phase 2 | |
| PEG-40 Hydrogenated Castor Oil, Trideceth-9 | 3.00 |
| Pentylene Glycol | 3.00 |
| Water, Pentylene Glycol, Glycerin, Sodium Lactate, Lactic Acid, Serine, Urea, Sorbitol, Sodium Chloride, Allantoin | 2.00 |
| Phase 3 | |
| Aminomethyl Propanol | 0.50 |
| Phase 4 | |
| Phenoxyethanol | 1.00 |
| Tropolone | 0.005 |

Formulation F8: Silicone Emulsion

| Raw Material | % weight |
|---|---|
| Phase 1 | |
| Potassium Cetyl Phosphate, Hydrogenated Palm Glycerides | 1.00 |

-continued

| Raw Material | % weight |
|---|---|
| Cyclohexasiloxane | 4.00 |
| Cetearyl Alcohol | 1.50 |
| Phenyl Trimethicone | 3.00 |
| Stearyl Heptanoate, Stearyl Caprylate | 3.00 |
| Dimethicone | 1.00 |
| Xanthan Gum | 0.20 |
| Isoamyl p-Methoxycinnamate | 5.00 |
| Phase 2 | |
| Water | 77.19 |
| Propylene Glycol | 3.00 |
| Phase 3 | |
| Farnesol | 0.10 |
| Menthyl Lactate | 0.50 |
| Phase 4 | |
| Phenoxyethanol | 0.50 |
| Tropolone | 0.005 |
| Phase 5 | |
| Rosemary oil | 0.005 |

Formulation F9: Hair Conditioner

| Raw Material | % weight |
|---|---|
| Phase 1 | |
| Water | 90.595 |
| Polyquaternium-7 | 1.00 |
| Cetearyl Alcohol, Glyceryl Stearate, Stearalkonium Chloride | 4.50 |
| Citric Acid | 0.20 |
| Phase 2 | |
| Caprylyl Glycol | 1.00 |
| Polysorbate 20 | 2.00 |
| Phase 3 | |
| Phenoxyethanol | 0.50 |
| Tropolone | 0.005 |
| Phase 4 | |
| Fragrance | 0.20 |

Formulation F10: Shampoo

| Raw Material | % weight |
|---|---|
| Phase 1 | |
| Water | 62.40 |
| Acrylates/C10–30 Alkyl Acrylate Crosspolymer | 0.60 |
| Sodium Hydroxide 15% solution | 0.10 |
| Phase 2 | |
| Disodium EDTA | 0.10 |
| Decylene Glycoll | 1.00 |
| Phase 4 | |
| Glycol Distearate, Laureth-4, Cocamidopropyl Betaine | 3.00 |
| Phase 4 | |
| Sodium Laureth Sulfate (2 mole, 53%) | 10.00 |
| Cocoamphoacetate | 5.00 |
| Ammonium Cocoyl Isethionate | 12.00 |
| Acetamide MEA | 1.00 |
| Palmitamide MEA | 0.50 |
| Phase 5 | |
| Phenoxyethanol | 1.00 |
| Tropolone | 0.01 |

Formulation F11: Anti-Perspirant Stick

| Raw Material | % weight |
|---|---|
| Phase 1 | |
| Stearyl Alcohol | 22.499 |
| Isopropyl Palmitate | 20.00 |
| Hydrogenated Castor Oil | 10.00 |
| Farnesol | 0.30 |
| Phase 2 | |
| Aluminum Zirconium Tetrachlorohydrex Glycine | 20.00 |
| Phase 3 | |
| Talc | 2.00 |
| Phase 4 | |
| Cyclpentasiloxane | 20.00 |
| Dimethiconol Beeswax | 5.00 |
| Phase 5 | |
| Phenoxyethanol | 0.20 |
| Tropolone | 0.001 |

Formulation F12: Lotion Base for Wet Wipes (Emulsion)

| Raw Material | % weight |
|---|---|
| Phase 1 | |
| Cetearyl Isononanoate, Ceteareth-20, Stearyl Alcohol, Glyceryl Stearate, Glycerin, Ceteareth-12, Cetyl Palmitate | 3.00 |
| Mineral Oil | 3.00 |
| Phase 2 | |
| Water | 84.99 |
| Glycerin | 0.50 |
| Propyleneglycol | 1.00 |
| Hydrolite-5 | 3.00 |
| Allantoin | 0.10 |
| Phase 3 | |
| Phenoxyethanol | 1.00 |
| Tropolone | 0.01 |
| Phase 4 | |
| Fragrance | 0.40 |

Formulation F13: Base for Wet Wipes (Solution)

| Raw Material | % weight |
|---|---|
| Phase 1 | |
| Water | 88.79 |
| Propyleneglycol | 8.00 |
| Citric Acid 10% | 0.10 |
| Phase 2 | |
| Solubilizer (PEG-40 Hydrogenated Castor Oil, Trideceth-9, Propylene Glycol Water) | 2.00 |
| Fragrance | 0.10 |
| Phenoxyethanol | 1.00 |
| Tropolone | 0.01 |

Formulation F14: Sunscreen Lotion

| Raw Material | % weight |
|---|---|
| Phase 1 | |
| Potassium Cetyl Phosphate, Hydrogenated Palm Glycerides | 1.00 |

| Raw Material | % weight |
|---|---|
| alpha-Bisabolol | 0.10 |
| Cetearyl Alcohol | 1.50 |
| Myristyl Myristate | 1.00 |
| Cetearyl Ethylhexanoate | 4.00 |
| Stearyl Heptanoate, Stearyl Caprylate | 1.00 |
| Cyclopentasiloxane, Cyclohexasiloxane | 0.50 |
| Butyl Methoxydibenzoylmethane (avobenzone) | 1.50 |
| 4-Methylbenzylidene Camphor | 1.50 |
| Ethylhexyl Methoxycinnamate (Neo Heliopan ® AV) | 8.00 |
| VP/Hexadecene Copolymer | 1.00 |
| Acrylates/C10–30 Alkyl Acrylate Crosspolymer | 0.10 |
| Phase 2 | |
| Water | Ad 100 |
| Phase 3 | |
| Sodium Hydroxide, 10% solution | 0.50 |
| Phase 4 | |
| Fragrance | 0.20 |
| Phase 5 | |
| Phenoxyethanol | 1.00 |
| Tropolone | 0.012 |

Formulation F15: Silicone Emulsion with High SPF

| Raw Material | % weight |
|---|---|
| Phase 1 | |
| Potassium Cetyl Phosphate, Hydrogenated Palm Glycerides | 1.00 |
| Cyclohexasiloxane | 4.00 |
| Cetearyl Alcohol | 1.50 |
| Phenyl Trimethicone | 3.00 |
| Stearyl Heptanoate, Stearyl Caprylate | 3.00 |
| Dimethicone | 1.00 |
| Xanthan Gum | 0.20 |
| Isoamyl p-Methoxycinnamate | 5.00 |
| p-Methoxycinnamic acid-2-ethylhexyl ester (Neo Heliopan ® AV) | 5.00 |
| Butyl Methoxydibenzoylmethane (avobenzone) | 0.50 |
| Phase 2 | |
| Water | Ad 100 |
| Pentylene Glycol (1,2-Pentanediol) | 1.50 |
| Phase 3 | |
| Phenoxyethanol | 0.60 |
| Tropolone | 0.01 |

Formulation F16: W/O Sunscreen Lotion with High SPF

| Raw Material | % weight |
|---|---|
| Phase 1 | |
| Polyglyceryl-2 Dipolyhydroxystearate | 3.00 |
| Glyceryl Oleate | 1.00 |
| Beeswax | 1.20 |
| Ethylhexyl Isononanoate | 2.00 |
| Caprylic/Capric Triglyceride | 3.00 |
| C 12–15 Alkyl Benzoate | 3.00 |
| Benzophenone-3 | 6.00 |
| Homosalate | 10.00 |
| Ethylhexyl Salicylate | 5.00 |
| Butyl Methoxydibenzoylmethane (avobenzone) | 3.00 |
| Ethylhexyl Methoxycinnamate | 7.50 |

| Raw Material | % weight |
|---|---|
| Phase 2 | |
| Water | Ad 100 |
| 1,2-Hexanediol | 0.25 |
| 1,2-Octanediol (Caprylyl Glycol) | 0.25 |
| Phase 3 | |
| Magnesium Sulfate | 0.70 |
| Phase 4 | |
| Sodium Chloride | 0.50 |
| Phase 5 | |
| Phenoxyethanol | 0.50 |
| Tropolone | 0.01 |

We claim:

1. Antimicrobial mixture comprising:
   (a) phenoxyethanol

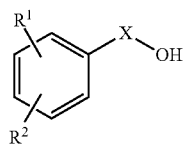

and
   (b) tropolone of the formula (II)

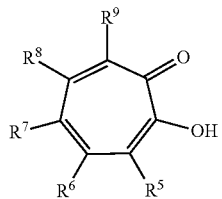

wherein the substituents $R^5$, $R^6$, $R^7$, $R^8$ and $R^9$ represent H, constituent (b) is present in an amount in the range of 0.001-10 wt. %, based on the amount of constituent (a), and compounds (a) and (b) are present in an amount such that an antimicrobial activity of said compounds (a) and (b) is synergistically intensified against *Aspergillus niger* as shown by a Kull value.

2. An antimicrobial mixture according to claim 1, wherein constituent (b) is present in an amount in the range of 0.5-4 wt. %, based on the amount of constituent (a).

3. An antimicrobial mixture according to claim 1, comprising one or more additional constituents (c) selected from the group consisting of (c) 2,4-hexadienoic acid (sorbic acid) and its salts, formaldehyde and paraformaldehyde, 2-hydroxybiphenyl ether and its salts, 2-zinc-sulfidopyridine N-oxide, inorganic sulfites and bisulfites, sodium iodate, chlorobutanolum, 4-ethylmercury-(II)5-amino-1,3-bis(2-hydroxybenzoic acid), its salts and esters, dehydracetic acid, formic acid, 1,6-bis(4-amidino-2-bromophenoxy)-n-hexane and its salts, the sodium salt of ethylmercury-(II)-thiosalicylic acid, phenylmercury and its salts, 10-undecylenic acid and its salts, 5-amino-1,3-bis(2-ethylhexyl)-5-methyl-hexahydropyrimidine, 5-bromo-5-nitro-1,3-dioxane, 2-bromo-2-nitro-1,3-propanediol, N-(4-chlorophenyl)-N'-(3,4-dichlorophenyl)-urea, 4-chloro-m-cresol, 2,4,4'-trichloro-2¹-hydroxy-diphenyl ether, 4-chloro-3,5-dimethylphenol, 1,1'-methylene-bis(3-(1-hydroxymethyl-2,4-dioximidazolidin-5-yl)urea), poly-(hexamethylenediguanide) hydrochloride, hexamethylenetetramine, 1-(3-chloroallyl)-3,5,7-triaza-1-azonia-adamantane chloride, 1-(4-chlorophenoxy)-1-(1H-imidazol-1-yl)-3,3-dimethyl-2-butanone, 1,3-bis(hydroxymethyl)-5,5-dimethyl-2,4-imidazolidinedione, 1,2-dibromo-2,4-dicyanobutane, benzethonium chloride, 2,2'-methylene-bis(6-bromo-4-chlorophenol),
bromochlorophene, mixture of 5-chloro-2-methyl-3(2H)-isothiazolinone and 2-methyl-3(2H)-isothiazolinone with magnesium chloride and magnesium nitrate, 2-benzyl-4-chlorophenol, 3-(4-Chlorphenoxy)-1,2-propanediol (Chlorphenesin), 2-chloroacetamide, chlorhexidine, chlorhexidine acetate, chlorhexidine gluconate, chlorhexidine hydrochloride, N-alkyl(C12-C22)trimethyl-ammonium bromide and chloride, 4,4-dimethyl-1,3-oxazolidine, N-hydroxymethyl-N-(1,3-di(hydroxymethyl)-2,5-dioxoimidazolidin-4-yl)-N'-hydroxy-methylurea, 1,6-bis(4-amidinophenoxy)-n-hexane and its salts, glutaraldehyde, 5-ethyl-1-aza-3,7-dioxabicyclo(3.3.0)octane, 3-(4-chlorophenoxy)-1,2-propanediol, hyamines, alkyl-($C_8$-$C_{18}$)-dimethyl-benzyl-ammonium chloride, alkyl-($C_8$-$C_{18}$)-dimethyl-benzylammonium bromide, alkyl-($C_8$-$C_{18}$)-dimethyl-benzyl-ammonium saccharinate, benzyl hemiformal, 3-iodo-2-propynyl butylcarbamate, sodium hydroxymethyl-aminoacetate and sodium hydroxymethyl-aminoacetate, imidazolidinylurea, diazolidinylurea, sodium hydroxymethylglycinate, chlorphenesin, DMDM hydantoin, methylchloroisothiazolinone, methylisothiazolinones, branched or unbranched 1,2-alkanediols having 6 to 12 carbon atoms, triclosan, climbazole, octoxyglycerol (ethylhexyl glycerol), Octopirox (1-hydroxy-4-methyl-6-(2,4,4-trimethylpentyl)-2 (1H)-pyridone, 2-aminoethanol), chitosan, totarol, farnesol, geranylacetol, glycerol monolaurate, arylalkyl alcohols (preferably 4-methyl-4-phenyl-2-pentanols, 2,2-dimethyl-3-phenylpropanol), essential oils with antimicrobial properties and isolates from essential oils with antimicrobial properties or single aroma chemicals with antimicrobial activity, and polyglycerol esters, preferably polyglyceryl 3-caprylates.

4. An antimicrobial mixture according to claim 1, wherein the amount of constituent (a) and/or the amount of constituent (b) in each case considered in itself is not antimicrobially active, but the total amount of constituent (a) and (b) is antimicrobially active.

5. A cosmetic or pharmaceutical formulation or foodstuff comprising the antimicrobial mixture according to claim 1.

6. A foodstuff according to claim 5, wherein the amount of constituent (a) and/or the amount of constituent (b) in each case considered in itself is not antimicrobially active, but the total amount of constituents (a) and (b) is antimicrobially active.

7. A method for the preservation or antimicrobial treatment of a perishable product, with the following step:
   bringing of the perishable product into contact with an antimicrobially active amount of the mixture according to claim 1.

8. A method for the cosmetic and/or therapeutic treatment of
   (i) microorganisms which cause body odour,
   (ii) microorganisms which cause acne and/or
   (iii) microorganisms which cause mycoses,
      comprising topical application of an antimicrobially active amount of the mixture according to claim 1.

9. An antimicrobial mixture according to claim 1, wherein the antimicrobial activity of said compounds (a) and (b) is synergistically intensified against the *Aspergillus niger* within two days.

10. An antimicrobial mixture according to claim 1, excluding antimicrobial mixtures comprising or consisting of
    (a) one or more branched or unbranched alkanediols having 6-12 carbon atoms,
    (b) tropolone, and
    (c) one or more preservatives selected from the group consisting of: benzoic acid, its esters and salts, salicylic acid and its salts, 2,4-dichlorobenzyl alcohol, 2-phenoxyethanol, benzyl alcohol, 1-phenoxy-propan-2-ol, 3-(4-chlorophenoxy)-1,2-propanediol and benzyl hemiformal.

* * * * *